United States Patent
Osborn

(10) Patent No.: US 8,193,000 B2
(45) Date of Patent: Jun. 5, 2012

(54) SCREENING TEST FOR BIODIESEL FUEL

(75) Inventor: Linda Osborn, Bargersville, IN (US)

(73) Assignee: Heritage Environmental Services, LLC, Indianapolis, IN (US)

( * ) Notice: Subject to any disclaimer, the term of this patent is extended or adjusted under 35 U.S.C. 154(b) by 0 days.

(21) Appl. No.: 12/336,701

(22) Filed: Dec. 17, 2008

(65) Prior Publication Data

US 2009/0155922 A1   Jun. 18, 2009

Related U.S. Application Data

(60) Provisional application No. 61/014,461, filed on Dec. 18, 2007.

(51) Int. Cl.
*G01N 21/00* (2006.01)

(52) U.S. Cl. .......... 436/164; 436/119; 436/139; 44/306; 44/307; 44/308

(58) Field of Classification Search .................. None
See application file for complete search history.

(56) References Cited

OTHER PUBLICATIONS

Rabinowitz, Joseph L. et al., Reutilization of fatty acid carbons for lung lipid synthesis, 1981, American Journal of physiology, vol. 240(4), E435-440.*

Bondioli, Paolo, The preparation of fatty acid esters by means of catalytic reactions, 2004, Topics in Catalysis, vol. 27, Nos. 1-4, pp. 77-82.*

Goff, M.J. et al, Acid-Catalyzed Alcoholysis of Soybean Oil, 2004, JAOCS, vol. 81(4), pp. 415-420.*

* cited by examiner

*Primary Examiner* — Yelena G Gakh
*Assistant Examiner* — Robert Xu
(74) *Attorney, Agent, or Firm* — Brinks Hofer Gilson & Lione

(57) ABSTRACT

A colorimetric test for determining the presence or absence of biodiesel in a diesel fuel sample. The colorimetric test involves adding concentrated sulfuric acid to a sample of diesel fuel and observing any color change of the sample. A darkening of the diesel fuel sample indicates the presence of biodiesel. The degree to which the color changes after the addition of the sulfuric acid is proportional to the amount of biodiesel in the sample and therefore can be used to determine the amount of biodiesel in the sample. The reagent(s), sample containers and any necessary color scale can be provided in a kit for field testing.

10 Claims, 2 Drawing Sheets

SCREENING TEST FOR BIODIESEL FUEL

RELATED APPLICATION

This application is based upon U.S. Provisional Patent Application Ser. No. 61/014,461 to which priority is claimed under 35 U.S.C. §120 and of which the entire specification is hereby expressly incorporated by reference.

TECHNICAL FIELD

The present invention relates to biodiesel fuels, including blends of biodiesel and diesel fuel. More particularly, the present invention is directed to a simple colorimetric test procedure for determining the presence of biodiesel in a fuel blend.

BACKGROUND ART

Diesel fuel is a refined petroleum product which historically has been burned in the engines powering most of the world's trains, ships, and large trucks. More recently, engines that burn diesel fuel have been adapted for use in light weight trucks and automobiles. Petroleum, from which diesel fuel is derived, is a non-renewable resource of finite supply. Acute shortages and dramatic price increases in petroleum and the refined products derived from petroleum have created the need to find alternative fuels. Moreover, diesel engines undesirably emit relatively high levels of certain pollutants, especially particulates. Accordingly, extensive research effort has focused on replacing some or all petroleum-based diesel fuel with a cleaner-burning fuel derived from a renewable source such as farm crops.

Biodiesel is the name for a variety of ester-based oxygenated fuels made from vegetable oils, fats, greases, or other sources of triglycerides. Biodiesel is a nontoxic and biodegradable substitute and supplement for petroleum diesel. Even in blends as low as 20% biodiesel to 80% petroleum diesel (B20), biodiesel can substantially reduce the emission levels and toxicity of diesel exhaust. Biodiesel has been designated as an alternative fuel by the United States Department of Energy and the United States Department of Transportation, and is registered with the United States Environmental Protection Agency (US EPA) as a fuel and fuel additive. Low blend concentrations of biodiesel (below 20%) can generally be used in any diesel engine, without the need for mechanical alterations, and is compatible with existing petroleum distribution infrastructure. For higher blends, typical modifications to diesel engines involve replacement of rubber fuel hoses and pump seals with a compatible elastomer.

Made from virgin or used vegetable oils and animal fats, biodiesel is methyl or ethyl esters of fatty acid. Although the US EPA has registered biodiesel as a fuel and fuel additive, currently there is no official tracking of biodiesel. The development, production and use of biodiesel are encouraged as a renewable energy source by tax incentives. In order to verify whether a given fuel blend is a biodiesel or qualifies as a biodiesel (for example for tax incentive qualification) it is necessary to quickly screen fuel blends to confirm the presence or absence of biodiesel.

Many countries, including the United States are advocating the use of biodiesel and are actively employing nearby resources to use for such purposes. Indiana, for example, can provide ample soy oil, whereas Thailand uses palm oil and Ireland uses frying oil and animal fats. Although the relative amounts vary, there are only five fatty acid chains that are common in most vegetable oils and animal fats. To be used as fuel, these fatty acids are chemically reacted (transesterified) with an alcohol, in the presence of a catalyst resulting in the formation of methyl or ethyl esters and glycerol. Used oils are can also be included in biodiesel but require more rigorous cleanup. Quality is essential for proper performance of the fuel with no damage to the engine. While an engine can be designed for 100% biodiesel, existing engines only tolerate from 5-20% biodiesel blends without modification or reduction in engine efficiency, although long-term use of biodiesel in engine research is still being studied.

In addition to being able to tell if a given quantity of fuel is a biodiesel for purposes of monitoring tax credit incentives, it is also important for someone purchasing a fuel to be able to confirm whether it is biodiesel or not, especially if one is paying a premium for biodiesel.

The present invention provides a simple colorimetric screening test to determine whether or a fuel contains biodiesel.

DISCLOSURE OF THE INVENTION

According to various features, characteristics and embodiments of the present invention which will become apparent as the description thereof proceeds, the present invention provides a method of determining the presence or absence of biodiesel in a diesel fuel which involves the steps of:
  a) providing a diesel fuel sample;
  b) adding sulfuric acid to the diesel fuel sample;
  c) observing any change in color of the diesel fuel sample after the addition of sulfuric acid; and
  d) determining, based upon the observation of a color change, the presence of biodiesel in the diesel fuel sample.

The present invention further provides a method of determining the amount of biodiesel in a diesel fuel which involves the steps of:
  a) providing a diesel fuel sample;
  b) adding sulfuric acid to the diesel fuel sample;
  c) observing any change in color of the diesel fuel sample after the addition of sulfuric acid; and
  d) determining, based upon the observation of a color change, the amount of biodiesel in the diesel fuel sample.

The present invention also provides a test kit for determining the presence or absence of biodiesel in a diesel fuel which comprises:
  a reference sample container for receiving a predetermined volume of a diesel fuel sample;
  a test sample container receiving a predetermined volume of a diesel fuel sample;
  means to collect and dispense diesel fuel samples into the reference sample container and the test sample container;
  a supply of sulfuric acid;
  means to dispense a test sample of diesel fuel the test sample container;
  and a color scale for observing any change in color of the diesel fuel sample after the addition of sulfuric acid and determining, based upon the observation of a color change, the presence of biodiesel in the diesel fuel sample.

BRIEF DESCRIPTION OF DRAWINGS

The present invention will be described with reference to the attached drawings which are given as non-limiting examples only, in which.

BEST MODE FOR CARRYING OUT THE INVENTION

Figure 1:
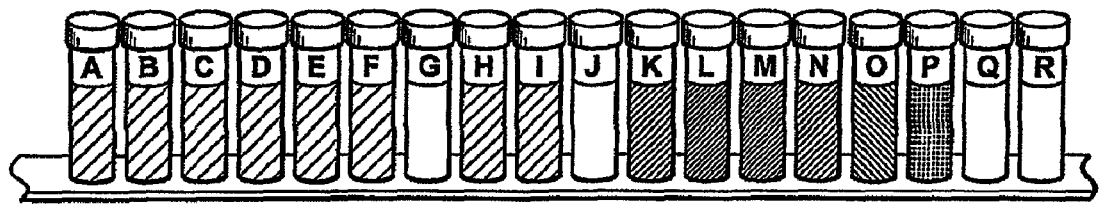
FIG. 1 depicts 18 different sample combinations of biodiesel and diesel fuel that range from 100% diesel fuel to 100% biodiesel prior to colorimetric reaction according to the present invention.

The present invention is directed to a simple calorimetric test procedure for determining the presence of biodiesel in a fuel blend. The test procedure of the present can be practiced easily in the field, laboratory or any desired location by merely combining the reagent(s) with a small biodiesel sample. A visual colorimetric comparison between the color of the sample before and after the reagent(s) is/are added readily indicates the presence or absence of biodiesel. The sensitivity and accuracy of the colorimetric test can be used to determine the presence of 1 percent by volume of biodiesel or less. The reagent(s) include sulfuric acid which is preferably added in a concentrated form, and a volumetric non-reactive filler solution such as hexadecane, as necessary, to provide a desired volume of sample to be tested.

Accordingly to one embodiment of the present invention the reagent(s) and sample containers can be provided in a test kit. The test kit can further include a neutral colored, e.g. white, background card or sheet in front or upon which the color of a reacted and non-reacted sample can be visually compared. The test kit can further include one or more color scales which can be used to determine the amount or percentage of biodiesel in a sample. For example, several color scales can be provided each having a base color which corresponds to no biodiesel. The proper or closest color scale can be selected by choosing the color scale having the base color which more closely matches the color of the non-reacted sample. Since the test kit and overall procedure is designed for field testing, the samples and reagent(s) are measured volumetrically. For purposes of the test kit, the reagents can be provided in pre-measured amounts. The test kit can further includes means such as pipettes, droppers, ampoules, and similar dispensing means to combine the reagent(s) with the sample, which generally involves adding the sample to the reagents in the test containers. It is to be understood that the sample can be added to the reagents or the reagents can be added to the sample. However, it is preferred to add the sample to the reagents in the test containers.

The present calorimetric screening test is based on the partial sulfonation process that occurs when sulfuric acid is mixed with biodiesel. In the presence of concentrated sulfuric acid ($H_2SO_4$), fatty acids and/or their methyl esters form surface-active α-sulfo fatty acids and/or methyl esters. When cold concentrated sulfuric acid reacts with the alkenes present in the biodiesel, alkylhydrogen sulfates are formed which are fairly soluble in the sulfuric acid. Some of the reaction products, however, are more soluble in the hydrocarbon phase/layer, producing a dark brown color.

Since diesel fuel is composed mainly of unbranched paraffins, the addition of sulfuric acid does not cause a darkening of the diesel fuel phase/layer. In fact, adding sulfuric acid may cause the diesel fuel phase/layer to become slightly lighter in color.

FIG. 1 depicts 18 different sample combinations of biodiesel and diesel fuel that range from 100% diesel fuel to 100% biodiesel prior to colorimetric reaction according to the present invention. The compositions of the samples, which are alphabetically labeled "A" through "R," are listed in Table 1 as follows:

TABLE 1

| Sample | % Biodiesel in Diesel Fuel | Source Comments Biodiesel:Diesel |
|---|---|---|
| A | 1% | Source 1:Source 1 |
| B | 2% | Source 1:Source 1 |
| C | 10% | Source 1:Source 1 |
| D | 20% | Source 1:Source 1 |
| E | 50% | Source 1:Source 1 |
| F | 75% | Source 1:Source 1 |
| G | 100% | Source 1:Source 1 |
| H | 2% | Source 2:Source 1 |
| I | 20% | Source 2:Source 1 |
| J | 100% | Source 2:Source 1 |
| K | 1% | Source 3:Source 1 |
| L | 20% | Source 3:Source 1 |
| M | 75% | Source 3:Source 1 |
| N | 0% | Diesel = Source 1 |
| O | 0% | Red-Dye Diesel: Source 1 |
| P | 50% | Source 1:Source 2 |
| Q | 0% | Low Sulfur Diesel: Source 2 |
| R | 50% | Source 1:Source 3 |

It is noted that the reference "source" herein is used to identify common biodiesel and diesel sources that were used to prepare the samples, but were not identified during the testing procedure.

Figure 2:
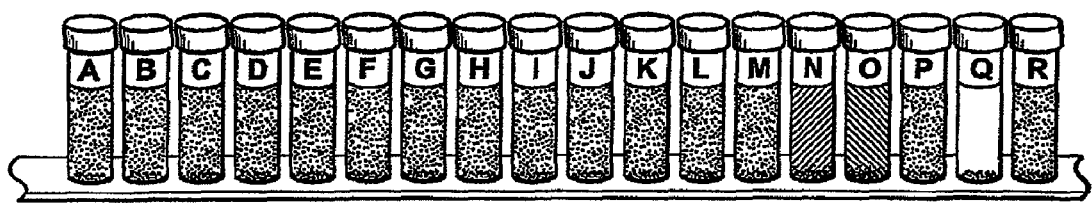
FIG. 2 depicts the 18 sample combinations of FIG. 1 after colorimetric reaction according to the present invention.

FIG. 2 depicts the 18 sample combinations of FIG. 1 after colorimetric reaction with sulfuric acid according to the present invention. As depicted, after the samples have been reacted with sulfuric acid, the only samples that have not undergone a dramatic color change are samples "N", "O" and "Q," which do not contain any biodiesel. All of the other samples, including sample "A" which contained only 1% biodiesel have turned a dark brown color. The procedure in which the samples have been reacted with sulfuric acid is described in the example below.

During the course of the present invention a typical biodiesel fuel sample was subjected to x-ray fluorescence (XRF) analysis which showed a sulfur concentration of 19 ppm. After the same biodiesel fuel was reacted with sulfuric acid and subjected to x-ray fluorescence (XRF) analysis, the sample showed a sulfur concentration of 1342 ppm after centrifugation. This significant increase in sulfur concentration and the corresponding/resulting change in color of reacted samples allows for easy visual determination of the presence of biodiesel in any fuel sample.

Figure 3:
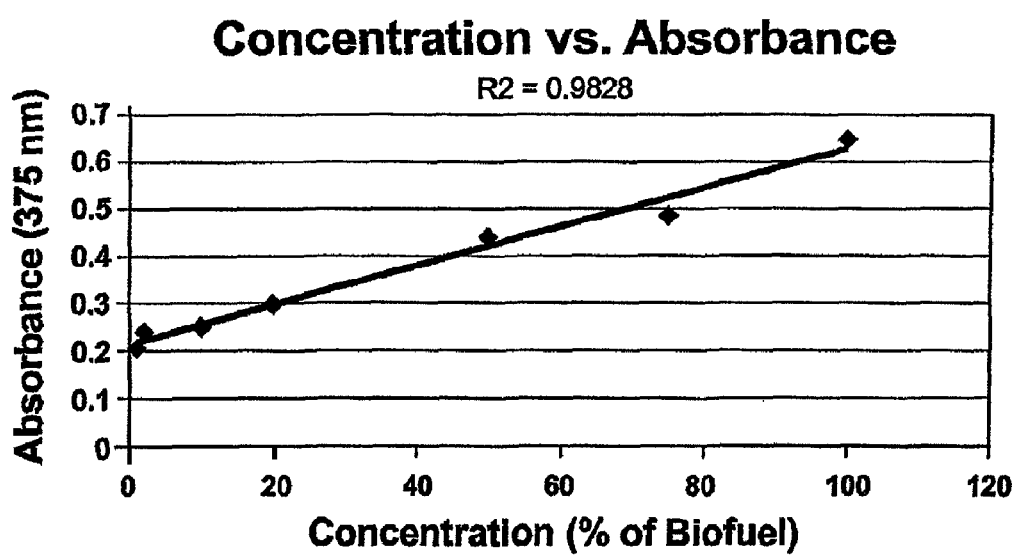
FIG. 3 is a spectrophotometric analysis of colorimetric reacted samples at an absorbance at 375 nm which shows a linear response ($r^2$=0.98) from concentrations ranging from 1 to 100 percent of biodiesel.

In addition to providing a clearly noticeable color change between reacted and non-reacted sample, it was discovered during the course of the present invention that the colorimetric reaction appears to occur in a quantitative manner. FIG. 3 is a spectrophotometric analysis of calorimetric reacted samples at an absorbance at 375 nm which shows a linear response ($r^2$=0.98) from concentrations ranging from 1 to 100 percent of biodiesel. This lineal response demonstrates that the calorimetric test procedure of the present invention can be used not only to determine the present of biodiesel, but can also be used to determine the amount of biodiesel in a given sample.

Three different sources of biodiesel were tested during the course of the present invention. From the results of the testing, it has been determined that the chemistries of all biodiesel fuels based on vegetable and animal oils are sufficiently similar so that the colorimetric screening test procedure of the present invention can be used to determine the presence or absence of biodiesel fuels from all types of sources of biodiesel.

Figure 4:
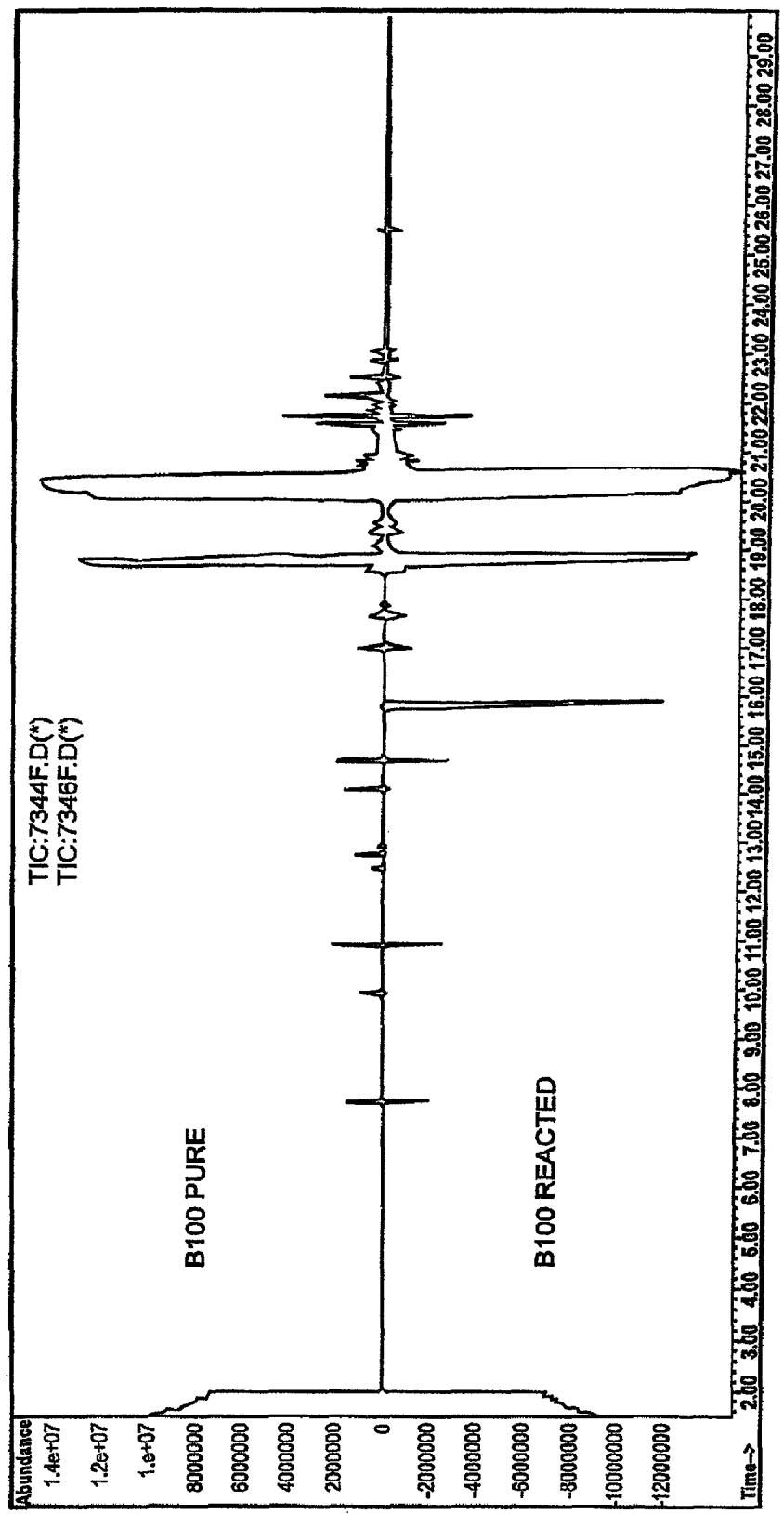
FIG. 4 depicts two chromatograms that show the differences between biodiesel before and after calorimetric reaction as analyzed by Gas Chromatography/Mass Spectroscopy.

FIG. 4 shows two chromatograms that are aligned in a mirror image that show the subtle differences between an unreacted biodiesel sample and a reacted biodiesel sample analyzed by Gas Chromatography/Mass Spectroscopy. As can be seen in FIG. 4, some of the trace levels of organic compounds (fatty acid methyl esters) are absent in the reacted sample (lower portion of graph). However, no additional chromatographable organic compounds appear to have been formed as a result of the reaction under these conditions (other than the $C_{16}$, which is added). The results confirm that the concentrated sulfuric acid reacts with the fatty acid methyl esters producing sulfates that are soluble in the sulfuric acid and other reaction products that are more soluble in the hydrocarbon phase/layer, producing the observed dark brown color.

The following example 1 is provided to demonstrate non-limiting features and characteristics of the present invention and to describe how the samples discussed in reference to FIGS. 1 and 2 were prepared. In this example and throughout the present disclosure percentages are by volume unless otherwise indicated.

EXAMPLE 1

The procedure for testing the samples in FIGS. 1 and 2 was as follows: 5 milliliters of each of the biodiesel/diesel fuel samples "A" through "R" where placed into small, non-reactive transparent reaction vessels containing 5 drops of concentrated sulfuric acid and 100 μL of hexadecane as a filler solution. The reaction vessels were sealed and gently inverted five times to mix the reactants with the samples. When added to samples that contain biodiesel, the sulfuric acid reacts with the double bonds that are present in the biodiesel. This reaction produces $SO_3$ which imparts a darkened color to the upper hydrocarbon layer. The degree of darkness of the color change is proportional to the amount of biodiesel in the sample. If the hydrocarbon fuel layer is lighter than or equal to the color of the original material, then the sample does not contain biodiesel. If the hydrocarbon fuel layer is darker than the original test sample, then biodiesel is present. Not only is the change or darkness of the color apparent when only a small amount of percentage of biodiesel is present, e.g. 1 percentage or even less, there is also a direct positive correlation between the amount of biodiesel present in the samples and the increase in visible discoloration of the sample. This correlation can be used to determine the amount or percent of biodiesel present in the samples.

EXAMPLE 2

This example sets for tests of 281 random samples of diesel fuel which were tested in Indiana. The random samples were obtained from 261 trucks and 20 retail fuel outlets. Of these random samples, 21 positive test results were obtained. Also 2 samples were too dark to test. The tests were conducted as set forth in Example 1 above. The results of the test are presented in Table 2 below:

TABLE 2

Results of Field Screening

| Sample | % Biodiesel |
|---|---|
| A | 1.5 |
| B | 2.2 |
| C | 1.3 |
| D | 4.2 |
| E | 2.2 |
| F | 2.0 |
| G | 3.7 |
| H | 7.7 |
| I | 6.7 |
| J | 6.4 |
| K | 2.0 |
| L | 6.2 |
| M | 5.9 |
| N | 3.4 |
| O | 3.9 |
| P | 1.2 |
| Q | 2.1 |
| R | 2.8 |
| S | 1.9 |
| T | 4.2 |
| U | 2.3 |

These field screening tests reveled that 7.5% of the samples contained biodiesel and that the average percentage of biodiesel in these samples was 3.5%. These field screening tests demonstrate the accuracy of the test procedure of the present invention.

It is understood that since the testing procedure of the present invention is a visual colorimetric test based upon the darkening of a fuel sample, it is more suitable for lighter colored fuel samples. However, in the case of darker fuel samples provisions can be made such as the use of narrow, thin or shallow sample containers which reduce the amount of sample that light has to pass through for purposes of establishing a base reference color.

Although the present invention has been described with reference to particular means, materials and embodiments, from the foregoing description, one skilled in the art can easily ascertain the essential characteristics of the present invention and various changes and modifications can be made to adapt the various uses and characteristics without departing from the spirit and scope of the present invention as set forth in the attached claims.

What is claimed is:

1. A field screening method of determining the presence or absence of biodiesel in a diesel fuel which comprises the steps of:
   a) providing a diesel fuel sample;
   b) combining sulfuric acid with the diesel fuel sample;
   c) observing any change in color of the diesel fuel sample after the diesel fuel sample is combined with the sulfuric acid; and
   d) determining, based upon the visual observation of a color change, the presence of biodiesel in the diesel fuel sample.

2. A field screening method of determining the presence or absence of biodiesel in a diesel fuel according to claim 1, wherein the diesel fuel sample in step a) is separated into two samples, including a test sample and a reference sample, wherein the test sample is added to the sulfuric acid in step b) and the color of the test sample and reference sample are compared in step c).

3. A field screening method of determining the presence or absence of biodiesel in a diesel fuel according to claim 1, wherein the amount of biodiesel in the diesel fuel sample is determined in step d).

4. A field screening method of determining the presence or absence of biodiesel in a diesel fuel according to claim 2, wherein the amount of biodiesel in the diesel fuel sample is determined in step d).

5. A field screening method of determining the presence or absence of biodiesel in a diesel fuel according to claim 1, wherein the steps are conducted in an indoor facility.

6. A field screening method of determining the presence or absence of biodiesel in a diesel fuel according to claim 1, wherein the determination in step d) of a color change the presence of biodiesel is performed using a colorimeter.

7. A field screening method of determining the amount of biodiesel in a diesel fuel which comprises the steps of:
   a) providing a diesel fuel sample;
   b) combining sulfuric acid with the diesel fuel sample;
   c) visually observing any change in color of the diesel fuel sample after the diesel fuel sample is combined with the sulfuric acid; and
   d) determining, based upon the observation of a color change, the amount of biodiesel in the diesel fuel sample.

8. A field screening method of determining the amount of biodiesel in a diesel fuel according to claim 7, wherein the diesel fuel sample in step a) is separated into two samples, including a test sample and a reference sample, wherein the test sample is added to the sulfuric acid in step b) and the color of the test sample and reference sample are compared in step c).

9. A field screening method of determining the amount of biodiesel in a diesel fuel according to claim 7, wherein the steps are conducted in an indoor facility.

10. A field screening method of determining the amount of biodiesel in a diesel fuel according to claim 1, wherein the determination in step d) of a color change the presence of biodiesel is performed using a colorimeter.

* * * * *